(12) United States Patent
Yamashita et al.

(10) Patent No.: US 8,781,793 B2
(45) Date of Patent: Jul. 15, 2014

(54) LIGHT EMISSION ANALYZING DEVICE

(75) Inventors: Masaki Yamashita, Hyogo (JP); Hiromi Mizukawa, Osaka (JP)

(73) Assignee: CREV Inc., Osaka (JP)

( * ) Notice: Subject to any disclaimer, the term of this patent is extended or adjusted under 35 U.S.C. 154(b) by 0 days.

(21) Appl. No.: 14/119,487

(22) PCT Filed: May 22, 2012

(86) PCT No.: PCT/JP2012/003326
§ 371 (c)(1),
(2), (4) Date: Nov. 22, 2013

(87) PCT Pub. No.: WO2012/160804
PCT Pub. Date: Nov. 29, 2012

(65) Prior Publication Data
US 2014/0107980 A1      Apr. 17, 2014

(30) Foreign Application Priority Data

May 25, 2011      (JP) .................................. 2011-117461

(51) Int. Cl.
| G01K 11/30 | (2006.01) |
| G01B 5/02 | (2006.01) |
| G01B 5/14 | (2006.01) |
| G01B 7/02 | (2006.01) |
| G01B 7/14 | (2006.01) |
| G01B 11/02 | (2006.01) |
| G01B 11/14 | (2006.01) |
| G01B 13/02 | (2006.01) |
| G01C 22/00 | (2006.01) |
| G01J 3/00 | (2006.01) |
| G01B 9/02 | (2006.01) |

(52) U.S. Cl.
USPC ........... 702/189; 702/134; 702/159; 702/172; 356/300; 356/484

(58) Field of Classification Search
USPC ........... 702/134, 159, 172, 189; 356/300, 484
See application file for complete search history.

(56) References Cited

U.S. PATENT DOCUMENTS

| 2002/0005159 A1* | 1/2002 | Kitagawa et al. ............... 117/13 |
| 2008/0063956 A1* | 3/2008 | Egashira ......................... 430/30 |
| 2011/0146756 A1* | 6/2011 | Sasaki et al. .................. 136/246 |

FOREIGN PATENT DOCUMENTS

| JP | 06-331547 | 12/1994 |
| JP | 2001-059772 | 3/2001 |

(Continued)

OTHER PUBLICATIONS

International Search Report issued Aug. 28, 2012 in International (PCT) Application No. PCT/JP2012/003326.

(Continued)

*Primary Examiner* — John Breene
*Assistant Examiner* — Manuel Rivera Vargas
(74) *Attorney, Agent, or Firm* — Wenderoth, Lind & Ponack, LLP.

(57) ABSTRACT

The light emission analyzing device includes: a first light intensity calculation unit that performs polynomial approximation on a spectroscopic spectrum indicating a light intensity for each wavelength in a container as measured by a spectrometer so as to calculate the light intensity; a second light intensity calculation unit that subtracts, for each wavelength, the light intensity calculated by the first light intensity calculation unit from the light intensity indicated by the spectroscopic spectrum measured by the spectrometer so as to calculate a light intensity corresponding to a bright-line spectrum of a molecule; and a ratio calculation unit that calculates, by using the light intensity calculated by the second light intensity calculation unit, a ratio between (a) a peak value of a molecular spectrum of a first molecule and (b) a peak value of a molecular spectrum of a second molecule.

13 Claims, 12 Drawing Sheets

(56) References Cited

FOREIGN PATENT DOCUMENTS

| | | |
|---|---|---|
| JP | 2004-296526 | 10/2004 |
| WO | 2010/024211 | 3/2010 |

OTHER PUBLICATIONS

Akihisa Matsuda, Control of Plasma Deposition by the Observation of Plasma Spectrum, Shinku, vol. 23, No. 6, 1980, pp. 277-282, with partial English translation.

Akihisa Matsuda, et al., Control of plasma chemistry for preparing highly stabilized amorphous silicon at high growth rate, Solar Energy Materials & Solar Cells, 2003, vol. 78, pp. 3-26.

Akihisa Matsuda, 2. Dissociation Process of Source Gas Materials in Silane Plasmas, Journal of Plasma and Fusion Research, vol. 76, No. 8, Aug. 2008, pp. 760-765, with partial English translation.

Lanxiang Sun, et al., Automatic estimation of varying continuum background emission in laser-induced breakdown spectroscopy, Spectrochimica Acta Part B, 2009, vo.64, pp. 278-287.

* cited by examiner

LIGHT EMISSION ANALYZING DEVICE

TECHNICAL FIELD

The present invention relates to light emission analyzing devices, and more particularly to a light emission analyzing device that analyzes a light emission state in a container measured by a spectrometer.

BACKGROUND ART

In forming films by using plasma Chemical Vapor Deposition (CVD) devices, it is important to suppress generation of fine particles called powder (for example, see Patent Literature (PTL) 1: Japanese Unexamined Patent Application Publication No. 2004-296526). The suppression of power generation requires measurement of a substrate temperature. However, it is difficult to directly measure the substrate temperature. In order to address this, a ratio of light emission intensities between a silicon* (Si*) film and a silan* (SiH*) film (where "*" represents an atomic valence) which are formed above the substrate is calculated as a value related to the substrate temperature. Such a conventional plasma CVD device controls a gas flow rate in the plasma CVD device to keep the calculated ratio constant, thereby suppressing the powder generation.

CITATION LIST

Patent Literature

[PTL 1] Japanese Unexamined Patent Application Publication No. 2004-296526

SUMMARY OF INVENTION

Technical Problem

However, in a plasma CVD device, there are not only a substrate but also a raw material gas in plasma state. The raw material gas emits light to make it difficult to observe only a light emission intensity of molecules or atoms (a molecular spectrum or atomic spectrum) in a certain thin film formed on the substrate. Therefore, it is difficult to correctly calculate a ratio of light emission intensities between specific two kinds of molecules or atoms.

This problem is occurred not only in plasma CVD devices, but also in any devices, such as spattering devices, etching devices, and sterilization monitoring devices, which need to calculate a ratio of light emission intensities between specific two kinds of molecules or atoms in a container.

In order to solve the above problems, an object of the present invention is to provide a light emission analyzing device capable of correctly calculating a ratio of light emission intensities between specific two kinds of molecules or atoms.

Solution to Problem

In accordance with an aspect of the present invention for achieving the object, there is provided a light emission analyzing device comprising: a first light intensity calculation unit configured to perform polynomial approximation on a spectroscopic spectrum indicating a light intensity for each wavelength in a container as measured by a spectrometer so as to calculate the light intensity; a second light intensity calculation unit configured to subtract, for each wavelength, the light intensity calculated by the first light intensity calculation unit from the light intensity indicated by the spectroscopic spectrum measured by the spectrometer so as to calculate a light intensity corresponding to a bright-line spectrum of a molecule or an atom; and a ratio calculation unit configured to calculate, by using the light intensity calculated by the second light intensity calculation unit, a ratio between (a) a peak value of a molecular spectrum of a first molecule or an atomic spectrum of a first atom and (b) a peak value of a molecular spectrum of a second molecule or an atomic spectrum of a second atom.

With the above structure, by performing polynomial approximation on a spectroscopic spectrum measured by a spectrometer, a light intensity is calculated for each wavelength. The light intensity applied with the polynomial approximation corresponds to a light intensity indicating thermal emission as a continuous spectrum. Therefore, by subtracting the intensity applied with the polynomial approximation from the light intensity indicated by the spectroscopic spectrum, it is possible to correctly calculate a light intensity of light emitted by a molecule or an atom. As a result, it is possible to correctly calculate a ratio of light emission intensities between specific two kinds of molecules or atoms.

It is possible that the first light intensity calculation unit is configured to perform the polynomial approximation on the spectroscopic spectrum indicating the light intensity for each wavelength in the container in a plasma Chemical Vapor Deposition (CVD) device as measured by the spectrometer so as to calculate, for each wavelength, a light intensity of light emitted by plasma in the plasma CVD device, and the second light intensity calculation unit is configured to subtract, for each wavelength, the light intensity of the light emitted by the plasma as calculated by the first light intensity calculation unit, from the light intensity indicated by the spectroscopic spectrum measured by the spectrometer so as to calculate a light intensity of light emitted by a molecule or an atom in a thin film formed above a substrate, the light intensity of the light emitted by the molecule or the atom corresponding to the bright-line spectrum of the molecule or the atom.

With the above structure, by performing polynomial approximation on a spectroscopic spectrum measured by a spectrometer, a light intensity of light emitted by plasma is calculated for each wavelength. Since plasma is light having a wide wavelength band, it is possible to approximate plasma by a polynomial. Therefore, by subtracting a light intensity of light emitted by the plasma approximated by the polynomial from the light intensity indicated by the spectroscopic spectrum measured by the spectrometer, it is possible to correctly calculate a light intensity of light emitted by a molecule or an atom in a thin film formed on/above the substrate. As a result, it is possible to correctly calculate a ratio of light emission intensities between specific two kinds of molecules or atoms.

It is also possible that the light emission analyzing device further includes a wavelength obtainment unit configured to obtain: a first wavelength; a second wavelength longer than the first wavelength; a third wavelength longer than the second wavelength; and a fourth wavelength longer than the third wavelength, wherein the first light intensity calculation unit is configured to (a) apply a predetermined function to (a-1) a spectroscopic spectrum included in a first wavelength band having the first wavelength to the second wavelength in the spectroscopic spectrum measured by the spectrometer and (a-2) a spectroscopic spectrum included in a second wavelength band having the third wavelength to the fourth wavelength in the spectroscopic spectrum measured by the spectrometer so as to calculate a light intensity of light in a third wavelength band that is a wavelength band from a first predetermined wavelength included in the first wavelength band to a second predetermined wavelength included in the second wavelength band, and (b) perform the polynomial approximation on (b-1) the light intensity calculated for the third wavelength band and (b-2) a spectroscopic spectrum in a wavelength band other than the third wavelength band so as to calculate the light intensity for each wavelength in the container.

The spectroscopic spectrum measured by the spectrometer includes (a) a spectroscopic spectrum indicating thermal emission as a continuous spectrum and (b) a bright-line spectrum of a molecule or an atom. Therefore, the spectroscopic spectrum measured by the spectrometer has a high light intensity at a wavelength corresponding to the bright-line spectrum. There is therefore the situation where, when polynomial approximation is performed on the spectroscopic spectrum measured by the spectrometer, due to values of the bright-line spectrum, it is impossible to correctly calculate, for each wavelength, the light intensity indicating thermal emission as a continuous spectrum. In order to address the above situation, a light intensity of light in the third wavelength band is calculated based on the first wavelength band and the second wavelength band which are located before and after the third wavelength band. Therefore, the spectroscopic spectrum indicating the thermal emission as a continuous spectrum can be correctly calculated. As a result, it is possible to correctly calculate a light intensity of light emitted by a molecule or an atom which corresponds to the bright-line spectrum, and eventually correctly calculate a ratio of light emission intensities between specific two kinds of molecules or atoms.

It is further preferable that the first light intensity calculation unit is further configured to (a) exclude a predetermined percentage of light intensities of respective wavelengths in descending order of a difference from a polynomial applied in the polynomial approximation, and (b) re-perform the polynomial approximation on (b-1) the light intensity calculated for the third wavelength band and (b-2) the spectroscopic spectrum in the wavelength band other than the third wavelength band.

By excluding an light intensity having a great difference from the polynomial, it is possible to correctly calculate the spectroscopic spectrum indicating the thermal emission as a continuous spectrum after removing influence of noises.

It is still further possible that the light emission analyzing device further includes a wavelength obtainment unit configured to obtain: a first wavelength; a second wavelength longer than the first wavelength; a third wavelength longer than the second wavelength; and a fourth wavelength longer than the third wavelength, wherein the first light intensity calculation unit is configured to apply a predetermined function to (a) a spectroscopic spectrum included in a first wavelength band having the first wavelength to the second wavelength in the spectroscopic spectrum measured by the spectrometer and (b) a spectroscopic spectrum included in a second wavelength band having the third wavelength to the fourth wavelength in the spectroscopic spectrum measured by the spectrometer so as to calculate a light intensity of light in a third wavelength band that is a wavelength band from a first predetermined wavelength included in the first wavelength band to a second predetermined wavelength included in the second wavelength band, and the second light intensity calculation unit is configured to subtract, for each wavelength in the third wavelength band, the light intensity calculated by the first light intensity calculation unit from the light intensity indicated by the spectroscopic spectrum measured by the spectrometer so as to calculate the light intensity corresponding to the bright-line spectrum of the molecule or the atom.

The spectroscopic spectrum measured by the spectrometer includes (a) a spectroscopic spectrum indicating thermal emission as a continuous spectrum and (b) a bright-line spectrum of a molecule or an atom. Therefore, the spectroscopic spectrum measured by the spectrometer has a high light intensity at a wavelength corresponding to the bright-line spectrum. There is therefore the situation where, when polynomial approximation is performed on the spectroscopic spectrum measured by the spectrometer, due to values of the bright-line spectrum, it is impossible to correctly calculate, for each wavelength, the light intensity indicating thermal emission as a continuous spectrum. In order to address the above situation, a light intensity of light in the third wavelength band is calculated based on the first wavelength band and the second wavelength band which are located before and after the third wavelength band. Therefore, the spectroscopic spectrum indicating the thermal emission as a continuous spectrum can be correctly calculated. As a result, it is possible to correctly calculate a light intensity of light emitted by a molecule or an atom which corresponds to the bright-line spectrum, and eventually correctly calculate a ratio of light emission intensities between specific two kinds of molecules or atoms.

It is still further possible, for example, that the first light intensity calculation unit is configured to (a) apply a straight line to a spectroscopic spectrum included in the first wavelength band having the first wavelength to the second wavelength in the spectroscopic spectrum measured by the spectrometer so as to calculate a first straight line, (b) apply a straight line to a spectroscopic spectrum included in the second wavelength band having the third wavelength to the fourth wavelength in the spectroscopic spectrum measured by the spectrometer so as to calculate a second straight line, and (c) generate a straight line from a point on the first predetermined wavelength on the first straight line to a point on the second predetermined wavelength on the second straight line so as to calculate a light intensity of light in the third wavelength band.

It is still further possible that the first predetermined wavelength is (the first wavelength+the second wavelength)/2, and the second predetermined wavelength is (the third wavelength+the fourth wavelength)/2.

It is still further possible that the first predetermined wavelength is the second wavelength, and the second predetermined wavelength is the third wavelength.

It should be noted that the present invention may be implemented not only as the light emission analyzing device including the above characteristic units, but also as: a light emission analyzing method including steps performed by the characteristic units included in the light emission analyzing device. The present invention may be implemented also as: a program causing a computer to serve as the characteristic units included in the light emission analyzing device; and a program causing a computer to execute the characteristic steps included in the light emission analyzing method. Of course, the program may be distributed via a non-transitory computer-readable recording medium such as a Compact Disc-Read Only Memory (CD-ROM) or via a communication network such as the Internet.

Advantageous Effects of Invention

The present invention can provide a light emission analyzing device capable of correctly calculating a ratio of light emission intensities between specific two kinds of molecules or atoms.

DESCRIPTION OF EMBODIMENTS

It should be noted that all the embodiments described below are specific examples of the present invention. Numerical values, shapes, materials, constituent elements, arrangement positions and the connection configuration of the constituent elements, steps, the order of the steps, and the like described in the following embodiments are merely examples, and are not intended to limit the present invention. Therefore, among the constituent elements in the following embodiments, constituent elements that are not described in independent claims that show the most generic concept of the present invention are described as elements constituting more desirable configurations, although such constituent elements are not necessarily required to achieve the object of the present invention.

Embodiment 1

The following describes a plasma CVD system according to Embodiment 1 of the present invention.

Figure 1:
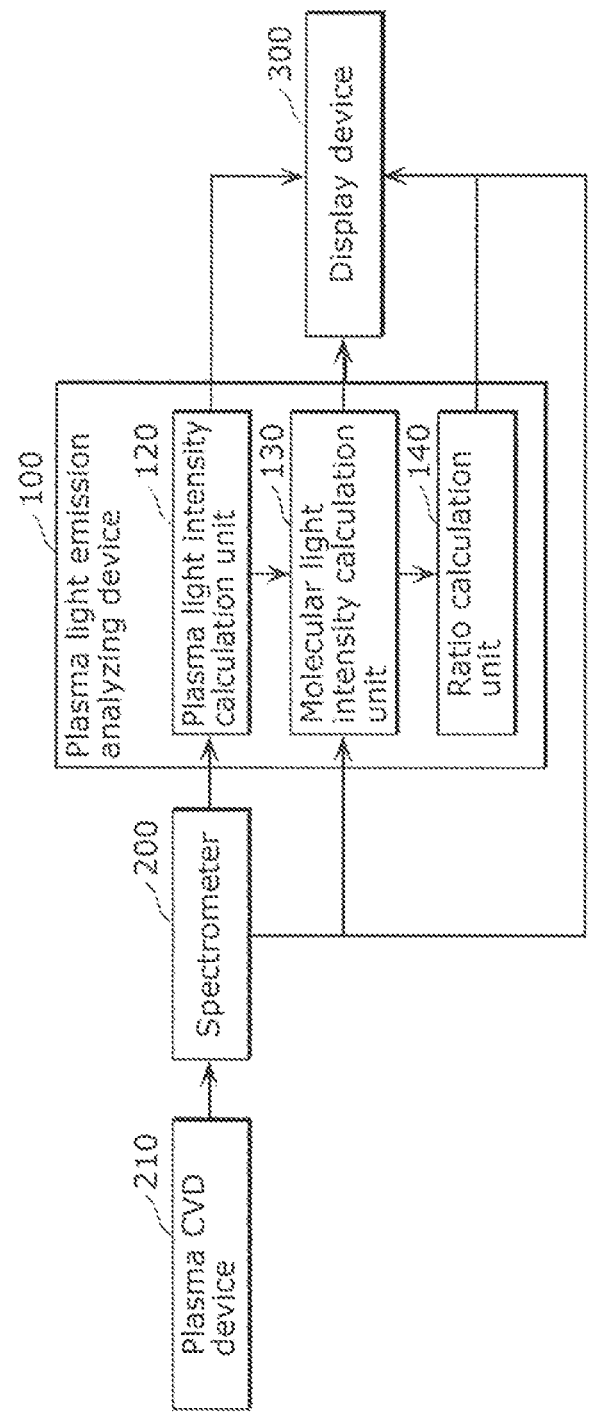
FIG. 1 is a block diagram showing a functional configuration of a plasma CVD system according to Embodiment 1 of the present invention.

FIG. 1 is a block diagram showing a functional configuration of the plasma CVD system according to Embodiment 1 of the present invention.

The plasma CVD system is a system that manufactures thin films on a substrate. The plasma CVD system includes a plasma CVD device 210, a spectrometer 200, a plasma light emission analyzing device 100, a display device 300.

The plasma CVD device 210 turns a material gas into plasma to form a thin film on/above a substrate. More specifically, the plasma CVD device 210 turns a material gas into plasma in a container to generate active excited molecules, radicals, and ions, thereby facilitating a chemical reaction. As a result, a thin film is formed on/above the substrate.

The spectrometer 200 measures a spectroscopic spectrum indicating a light intensity for each wavelength in the plasma CVD device 210.

The plasma light emission analyzing device 100 is an example of a light emission analyzing device that analyzes a light emission state in a container. The plasma light emission analyzing device 100 analyzes a light emission state of plasma in a container of the plasma CVD device 210.

The display device 300 is a device that displays the spectroscopic spectrum measured by the spectrometer 200, or results of analysis performed by the plasma light emission analyzing device 100.

The plasma CVD device 210, the spectrometer 200, and the display device 300 may be implemented by using known techniques, so that they are not described here in detail.

The plasma light emission analyzing device 100 includes a plasma light intensity calculation unit 120, a molecular light intensity calculation unit 130, and a ratio calculation unit 140.

The plasma light intensity calculation unit 120 is an example of a first light intensity calculation unit that performs polynomial approximation on a spectroscopic spectrum indicating the light intensity for each wavelength in the container as measured by the spectrometer 200 so as to calculate the light intensity for each wavelength in the container. For example, the plasma light intensity calculation unit 120 performs polynomial approximation on a spectroscopic spectrum indicating a light intensity for each wavelength in the plasma CVD device 210 as measured by the spectrometer 200 so as to calculate a light intensity indicating thermal emission as a continuous spectrum continuing in a wavelength direction, in other words, a light intensity for each wavelength of light emitted by plasma in the plasma CVD device 210.

The molecular light intensity calculation unit 130 is an example of a second light intensity calculation unit that subtracts, for each wavelength, the light intensity calculated by the plasma light intensity calculation unit 120 from the light intensity indicated by the spectroscopic spectrum so as to calculate a light intensity corresponding to a bright-line spectrum of a molecule or an atom. For example, the molecular light intensity calculation unit 130 subtracts, for each wavelength, the light intensity of the light emitted by the plasma as calculated by the plasma light intensity calculation unit 120 from the light intensity indicated by the spectroscopic spectrum so as to calculate a light intensity of light emitted by a molecule in a thin film formed on/above the substrate.

The ratio calculation unit 140 calculates, by using the light intensity calculated by the molecular light intensity calculation unit 130, a ratio between a peak value of a molecular spectrum of a first molecule and a peak value of a molecular spectrum of a second molecule. Hereinafter, the ratio calculated by the ratio calculation unit 140 is assumed to be a ratio between molecular spectrums. However, the ratio calculated by the ratio calculation unit 140 is not limited to the ratio between molecular spectrums. For example, the ratio calculation unit 140 may calculate a ration between an atomic spectrum and a molecular spectrum, or a ratio between atomic spectrums.

The following describes processing performed by the plasma light emission analyzing device 100 with reference to examples.

Figure 2:
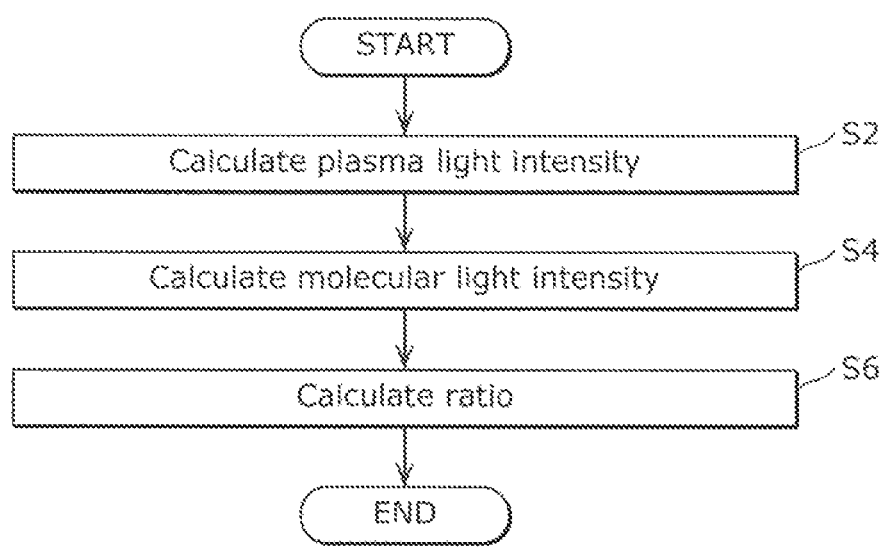
FIG. 2 is a flowchart of processing performed by a plasma light emission analyzing device.

FIG. 2 is a flowchart of the processing performed by the plasma light emission analyzing device 100.

The plasma light intensity calculation unit 120 performs polynomial approximation on a spectroscopic spectrum indicating a light intensity for each wavelength in the plasma CVD device 210 as measured by the spectrometer 200 so as to calculate, for each wavelength, a light intensity of light emitted by plasma in the plasma CVD device 210 (S2). The light emitted by the plasma indicates thermal emission as a continuous spectrum.

Figure 3:
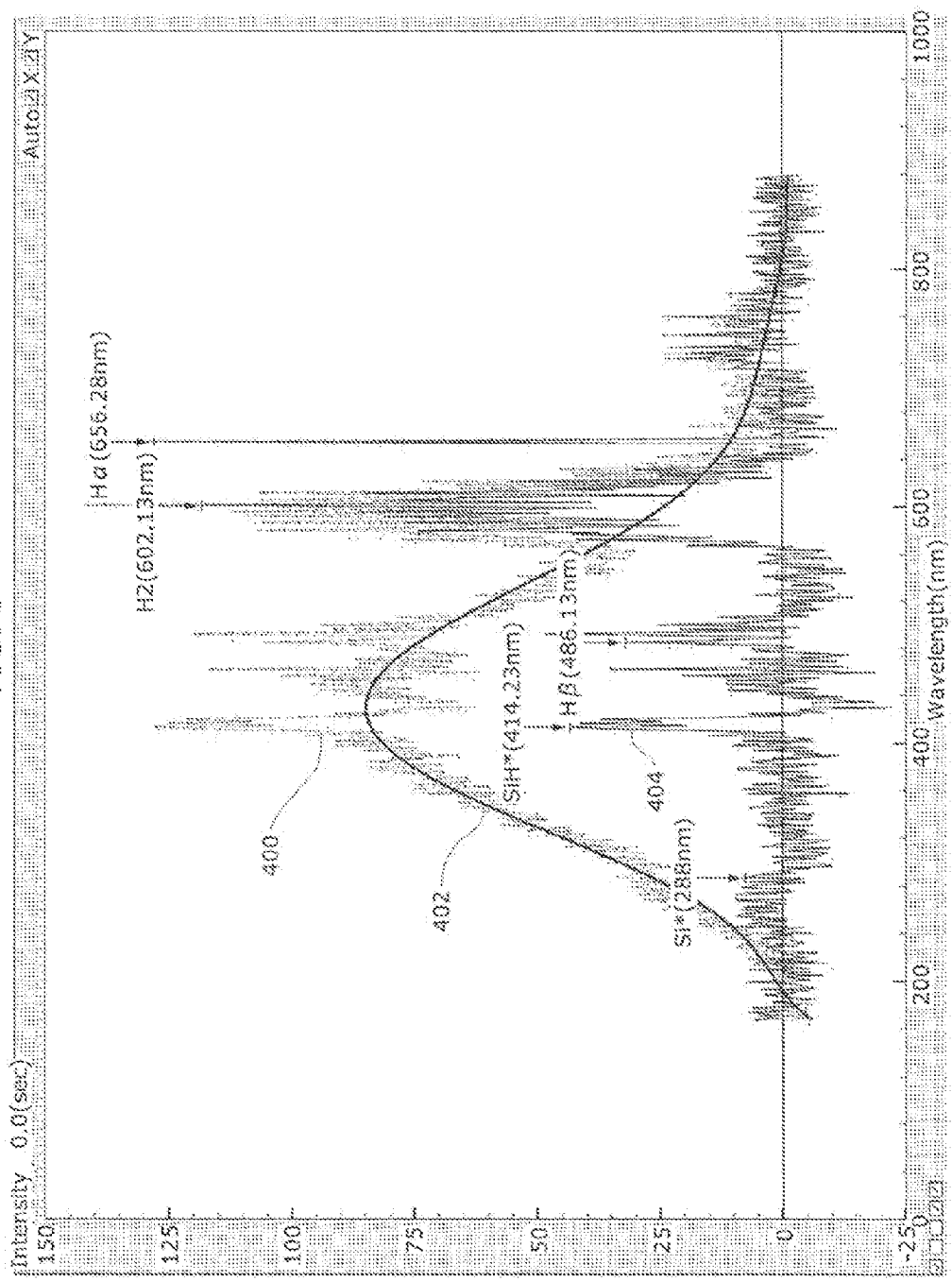
FIG. 3 is a graph showing an example of image displayed by a display device.

FIG. 3 is a graph showing an example of image displayed by the display device 300. In the figure, a horizontal axis indicates a wavelength, and a vertical axis indicates a light intensity. For example, by using the method of least squares, the plasma light intensity calculation unit 120 applies, for example, a nine-dimensional polynomial to a spectroscopic spectrum 400 measured by the spectrometer 200. As a result, a waveform 402 is obtained. The waveform 402 indicates a light intensity of thermal emission as a continuous spectrum, in other words, the waveform 402 indicates, for each wavelength, a light intensity of light emitted by plasma in the plasma CVD device 210. The light emitted by the plasma is emitted when a material gas is turned into the plasma. Such light may be emitted, for example, in either or both cases where $SiH_4$ as a molecular of a thin film formed on/above the substrate is separated into atoms and then re-combined and where electrons released from $SiH_4$ bump into $SiH_4$.

Next, the molecular light intensity calculation unit 130 subtracts, for each wavelength, the light intensity of the light emitted by the plasma as calculated by the plasma light intensity calculation unit 120 from the light intensity indicated by the spectroscopic spectrum so as to calculate a light intensity of light emitted by a molecule in a thin film formed on/above the substrate (S4). This light intensity corresponds to a bright-line spectrum of a molecule or an atom.

Figure 4:
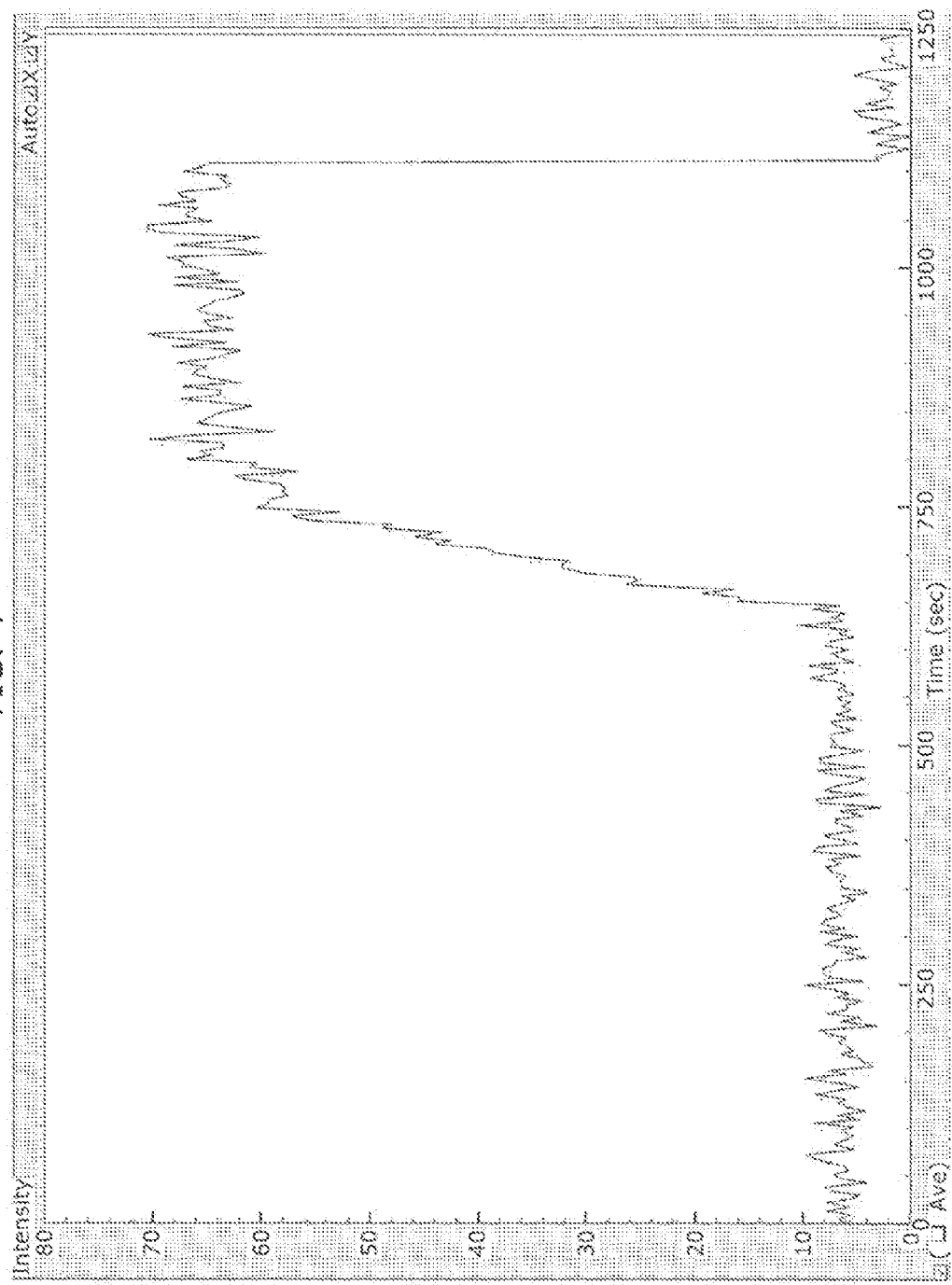
FIG. 4 is a graph plotting a temporal transition of an intensity of light emitted by SiH*.

For example, referring to FIG. 3, the molecular light intensity calculation unit 130 subtracts, for each wavelength, a light intensity indicated by the waveform 402 from a light intensity indicated by the spectroscopic spectrum 400, thereby obtaining a waveform 404. The waveform 404 indicates a light intensity of light emitted by a molecule in the thin film formed on/above the substrate. For example, when SiH* has a peak light intensity at a wavelength of 414.23 nm, the light intensity is approximately 43. FIG. 4 is a graph plotting a temporal transition of the light intensity of light emitted by SiH*. In the graph, a horizontal axis indicates a time, and a vertical axis indicates a light intensity.

Finally, the ratio calculation unit 140 calculates, by using the light intensity calculated by the molecular light intensity calculation unit 130, a ratio between a peak value of a molecular spectrum of a first molecule and a peak value of a molecular spectrum of a second molecule (S6).

Figure 5:
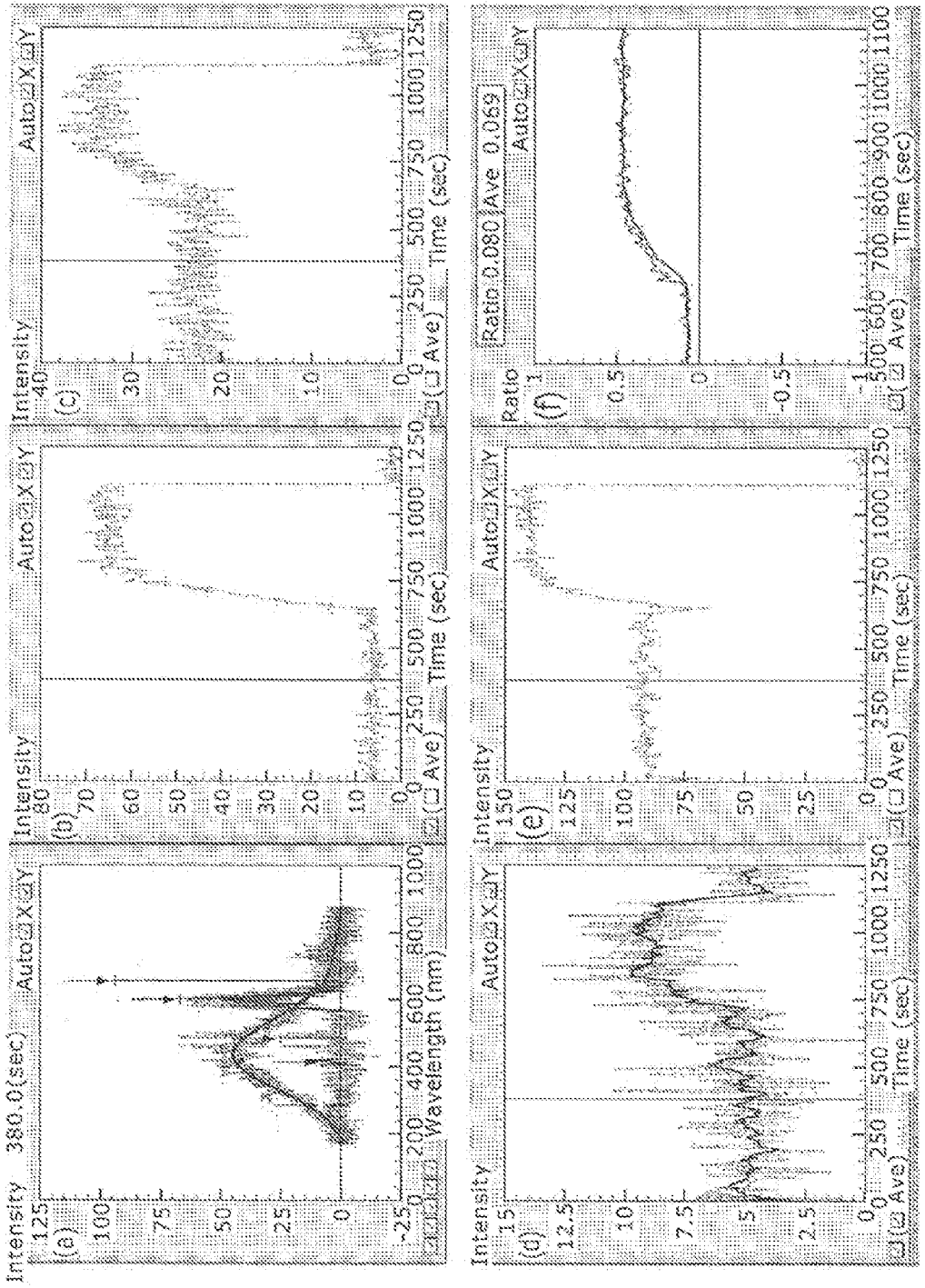
FIG. 5 shows graphs plotting results of various analyses performed by the plasma light emission analyzing device.

For example, referring to FIG. 3, the ratio calculation unit 140 calculates a ratio between a light intensity of SiH* and a light intensity of Hα. The light intensity of Hα indicates a light intensity of an Hα line at a wavelength of 656.28 nm among line spectra of a hydrogen atom. FIG. 5 shows graphs plotting results of various analyses performed by the plasma light emission analyzing device 100. (f) in FIG. 5 is a graph plotting a temporal change of a ratio between a light intensity of SiH* and a light intensity of Hα. In the graph, a horizontal axis indicates a time, and a vertical axis indicates the ratio, (f) in FIG. 5 also shows that a value of a current ratio is 0.080 and a value of an average ratio is 0.069. It should be noted that the graph (a) in FIG. 5 is the same as FIG. 3 and the graph (b) in FIG. 5 is the same as FIG. 4. (c) in FIG. 5 is a graph plotting a temporal change of a light intensity of Hβ. (d) in FIG. 5 is a graph plotting a temporal change of a light intensity of Si*. (e) in FIG. 5 is a graph plotting a temporal change of a light intensity of Hα. In each of the graphs, a horizontal axis indicates a time, and a vertical axis indicates a light intensity. The light intensity of Hβ indicates a light intensity of an Hβ line at a wavelength of 486.13 nm among line spectra of a hydrogen atom.

As described above, the plasma light emission analyzing device 100 according to Embodiment 1 performs polynomial approximation on a spectroscopic spectrum measured by the spectrometer 200 so as to calculate, for each wavelength, a light intensity of light emitted by plasma. Since plasma is light that indicates thermal emission as a continuous spectrum and has a wide wavelength band, it is possible to approximate plasma by a polynomial. Therefore, by subtracting a light intensity of light emitted by the plasma approximated by a polynomial from the light intensity indicated by the spectroscopic spectrum, it is possible to correctly calculate a light intensity of light emitted by a molecule or an atom in a thin film formed on/above the substrate. It is therefore possible to correctly calculate a ratio of light emission intensities between specific two kinds of molecules. As a result, is it possible to control a gas flow rate in the plasma CVD device 210 to suppress generation of powder.

Embodiment 2

Next, the description is given for a plasma CVD system according to Embodiment 2 of the present invention.

The plasma CVD system according to Embodiment 2 differs from the plasma CVD system according to Embodiment 1 in that a light intensity in a predetermined wavelength band is excluded from a spectroscopic spectrum in the plasma CVD device 210 as measured by the spectrometer 200, and polynomial approximation is performed on the spectroscopic spectrum not including the light intensity. The following describes mainly the differences from Embodiment 1.

Figure 6:
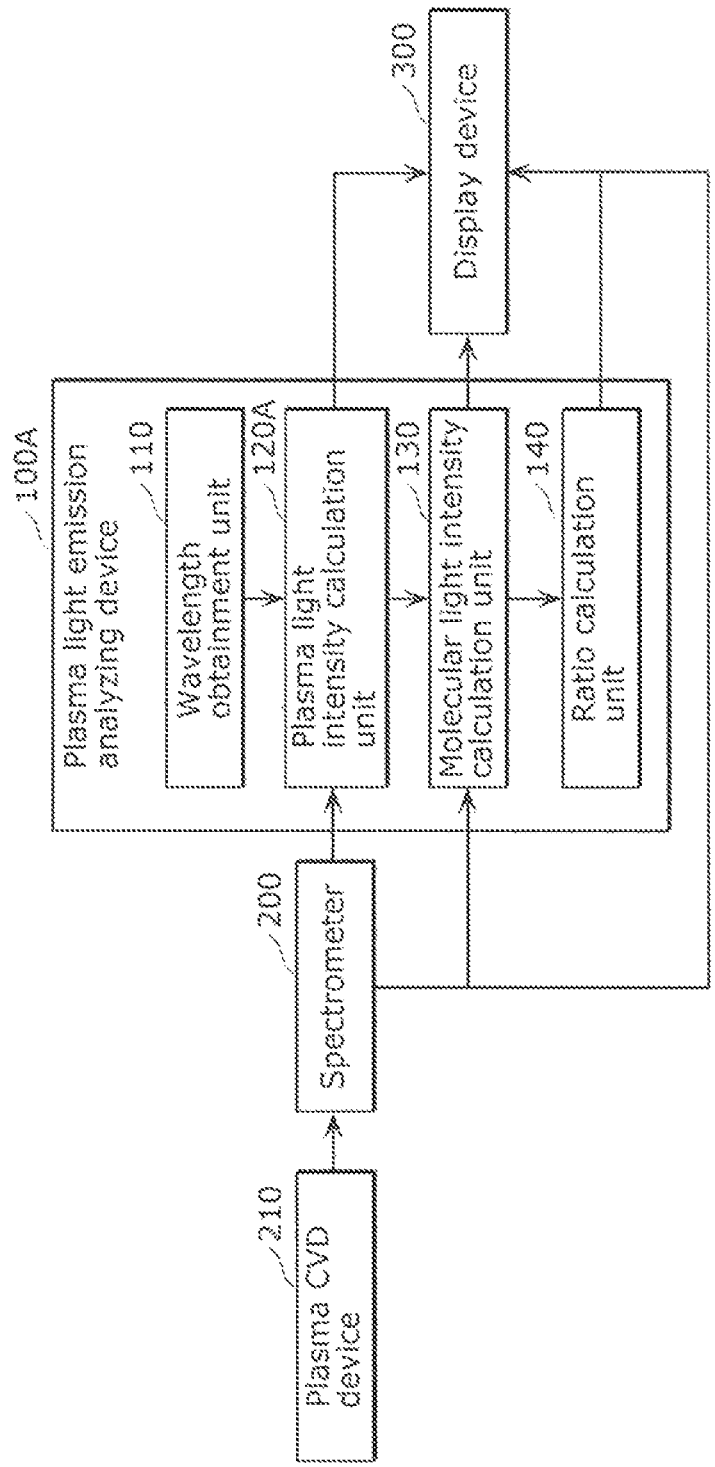
FIG. 6 is a block diagram showing a functional configuration of a plasma CVD system according to Embodiment 2 of the present invention.

FIG. 6 is a block diagram showing a functional configuration of the plasma CVD system according to Embodiment 2 of the present invention. Hereinafter, the same reference numerals in the plasma CVD system according to Embodiment 1 are assigned to identical structural elements in the other figures. The identical structural elements share the same name and the same function, so that their detailed explanations are not repeated below.

The plasma CVD system is a system that forms thin films on/above the substrate. The plasma CVD system includes the plasma CVD device 210, the spectrometer 200, a plasma light emission analyzing device 100A, and the display device 300.

The plasma light emission analyzing device 100A is a device that analyzes a light emission state of plasma in the plasma CVD device 210. The plasma light emission analyzing device 100A includes the wavelength obtainment unit 110, a plasma light intensity calculation unit 120A, the molecular light intensity calculation unit 130, and the ratio calculation unit 140.

The wavelength obtainment unit 110 obtains: a first wavelength; a second wavelength longer than the first wavelength; a third wavelength longer than the second wavelength; and a fourth wavelength longer than the third wavelength. The wavelength obtainment unit 110 may obtain values of the respective wavelengths by receiving the values inputted by a user using a keyboard, or by receiving the values from a storage device in which the values are previously stored.

The plasma light intensity calculation unit 120A is an example of the first light intensity calculation unit. The plasma light intensity calculation unit 120A (a) applies a predetermined function to (a-1) a spectroscopic spectrum included in a first wavelength band having the first wavelength to the second wavelength in the spectroscopic spectrum measured by the spectrometer 200 and (a-2) a spectroscopic spectrum included in a second wavelength band having the third wavelength to the fourth wavelength in the spectroscopic spectrum measured by the spectrometer 200 so as to calculate a light intensity of light in a third wavelength band that is a wavelength band from a first predetermined wavelength included in the first wavelength band to a second predetermined wavelength included in the second wavelength band. In addition, the plasma light intensity calculation unit 120A (b) performs the polynomial approximation on (b-1) the light intensity calculated for the third wavelength band and (b-2) a spectroscopic spectrum in a wavelength band other than the third wavelength band so as to calculate, for each wavelength, the light intensity of light emitted by plasma in the plasma CVD device 210. More specifically, the plasma light intensity calculation unit 120A (a) applies a straight line to a spectroscopic spectrum included in the first wavelength band having the first wavelength to the second wavelength in the spectroscopic spectrum measured by the spectrometer 200 so as to calculate a first straight line, (b) applies a straight line to a spectroscopic spectrum included in the second wavelength band having the third wavelength to the fourth wavelength in the spectroscopic spectrum measured by the spectrometer 200 so as to calculate a second straight line, and (c) generates a straight line from a point on the first predetermined wavelength on the first straight line to a point on the second predetermined wavelength on the second straight line so as to calculate a light intensity of light in the third wavelength band. Here, the first predetermined wavelength is (the first wavelength+the second wavelength)/2, and the second predetermined wavelength is (the third wavelength+the fourth wavelength)/2.

The following describes processing performed by the plasma light emission analyzing device 100A with reference to examples.

Figure 7:
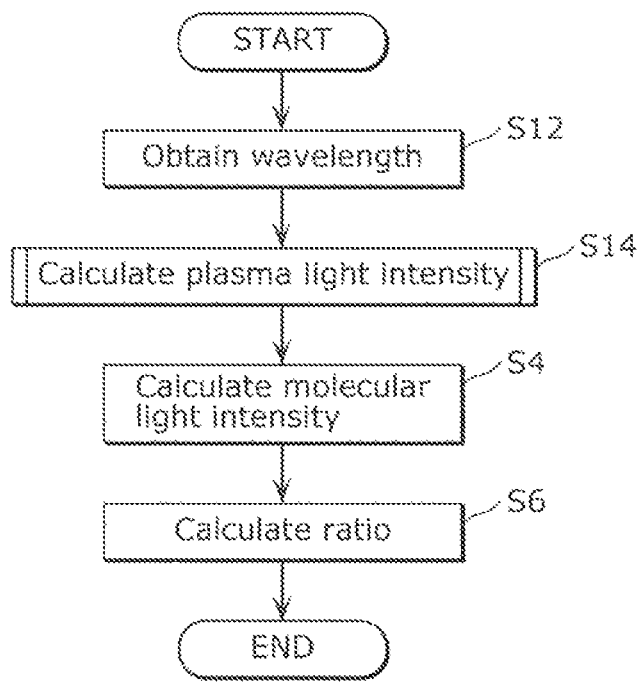
FIG. 7 is a flowchart of processing performed by a plasma light emission analyzing device.

FIG. 7 is a flowchart of the processing performed by the plasma light emission analyzing device 100A.

The wavelength obtainment unit 110 obtains: a first wavelength; a second wavelength longer than the first wavelength; a third wavelength longer than the second wavelength; and a fourth wavelength longer than the third wavelength (S12). For example, in the spectroscopic spectrum graph shown in FIG. 8, it is assumed that a first wavelength X1, a second wavelength X2, a third wavelength X3, and a fourth wavelength X4 are obtained.

The plasma light intensity calculation unit 120A performs polynomial approximation on a spectroscopic spectrum indicating the light intensity for each wavelength in the plasma CVD device 210 as measured by the spectrometer 200 so as to calculate a light intensity indicating thermal emission as a continuous spectrum continuing in a wavelength direction, in other words, calculating, for each wavelength, a light intensity of light emitted by plasma in the plasma CVD device 210 (S14).

Figure 8:
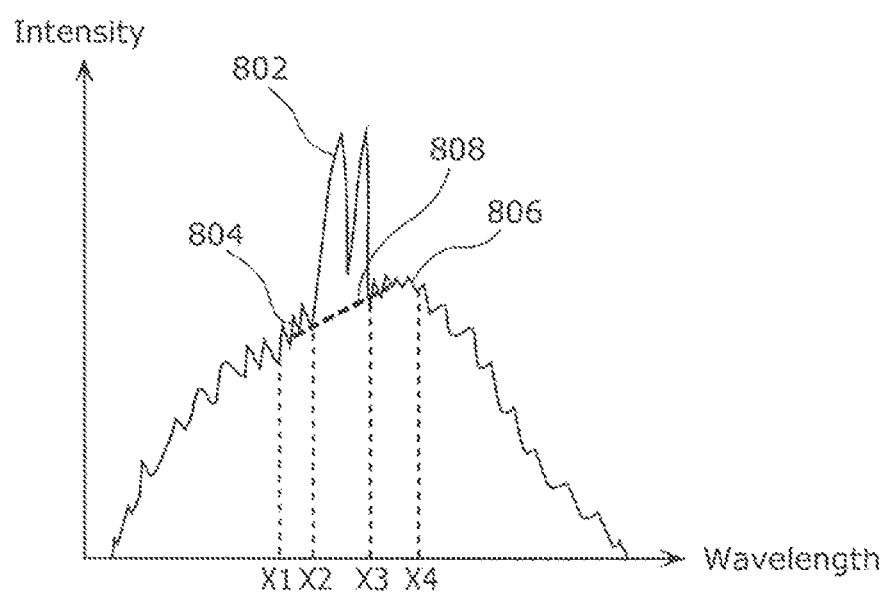
FIG. 8 is a graph of a spectroscopic spectrum.
Figure 9:
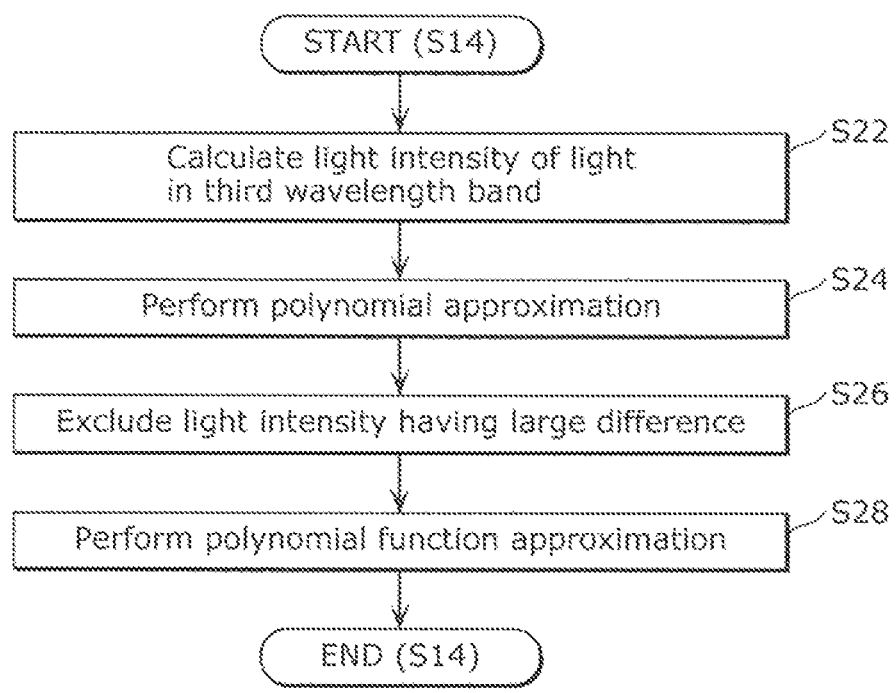
FIG. 9 is a flowchart of details of the plasma light intensity calculation (S14 in FIG. 7).

FIG. 9 is a flowchart of details of the plasma light intensity calculation (S14 in FIG. 7). The following describes the plasma light intensity calculation (S14 in FIG. 7) by presenting examples, with reference to the spectroscopic spectrum graph shown in FIG. 8.

Referring to FIG. 8, the plasma light intensity calculation unit 120A applies a straight line 808 to a spectroscopic spectrum 804 included in the first wavelength band (wavelength X1 to X2) and a spectroscopic spectrum 806 included in the second wavelength band (wavelength X3 to X4) among a spectroscopic spectrum 802 measured by the spectrometer 200 so as to calculate a light intensity of light in the third wavelength band (wavelength (X1+X2)/2 to (X3+X4)/2) (S22). The application of the straight line is performed as follows. The plasma light intensity calculation unit 120A applies a straight line to the spectroscopic spectrum 804 included in the first wavelength band (wavelength X1 to X2) by using the method of least squares, so that a point on the applied straight line which divides the wavelength into two wavelengths each having (X1+X2)/2 is determined as the first midpoint. Likewise, the plasma light intensity calculation unit 120A applies a straight line to the spectroscopic spectrum 806 included in the second wavelength band (wavelength X3 to X4) by using the method of least squares, so that a point where a point on the applied straight line which divides the wavelength into two wavelengths each having (X3+X4)/2 is determined as the second midpoint. Then, the plasma light intensity calculation unit 120A calculates a straight line 808 from the first midpoint to the second midpoint, as a straight line indicating a light intensity of light in the third wavelength band (wavelength (X1+X2)/2 to (X3+X4)/2). It should be noted that the application of a straight line is not limited to the above method. For example, it is also possible that the straight line 808 is applied to the spectroscopic spectra 804 and 806 by using the method of least squares, so that the sum of squares of the distance between the straight line 808 and each of the spectroscopic spectra 804 and 806 is minimized. In this case, the third wavelength band may be a wavelength X2 to X3.

It should also be noted that the third wavelength band is not limited to the above. The third wavelength band may be any other wavelength band as long as the third wavelength band is a wavelength band from a first predetermined wavelength included in the first wavelength band to a second predetermined wavelength included in the second wavelength band.

The plasma light intensity calculation unit 120A performs polynomial approximation on (a) a light intensity calculated for the third wavelength band and (b) a spectroscopic spectrum in a wavelength band other than the third wavelength band so as to calculate, for each wavelength, a light intensity of light emitted by plasma in the plasma CVD device 210 (S24). More specifically, the plasma light intensity calculation unit 120A performs polynomial approximation on a spectroscopic spectrum that is generated by replacing values in the third wavelength band (wavelength (X1+X2)/2 to (X3+X4)/2) in the spectroscopic spectrum 802 to the straight line 808.

Figure 10:
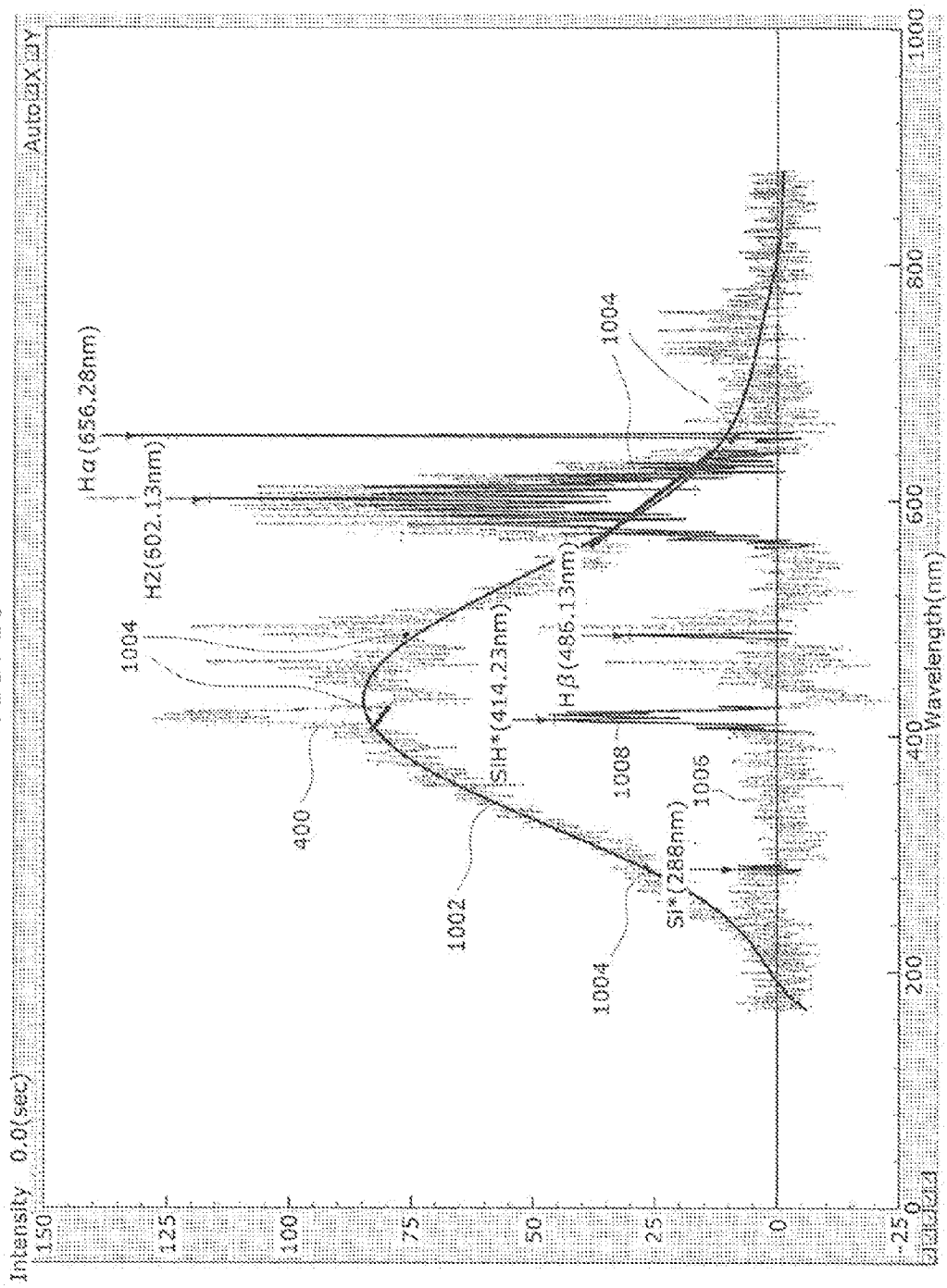
FIG. 10 is a graph for explaining the polynomial approximation (S24 in FIG. 9).

FIG. 10 is a graph for explaining the polynomial approximation (S24 in FIG. 9). In the graph, a horizontal axis indicates a wavelength, and a vertical axis indicates a light intensity. The graph shown in FIG. 10 shows a plurality of the third wavelength bands, and also shows straight lines 1004 each of which is the straight line 808 calculated at S22 for a corresponding one of the third wavelength bands. For example, for each of the third wavelength bands, by using the method of least squares, the plasma light intensity calculation unit 120A applies, for example, a nine-dimensional polynomial to (a) the straight line 1004 in the third wavelength band and (b) a spectroscopic spectrum 400 in the wavelength band other than the third wavelength band. As a result, a waveform 1002 is obtained.

Next, the plasma light intensity calculation unit 120A excludes a predetermined percentage of light intensities of the respective wavelengths in descending order of a difference from the applied polynomial (S26). For example, the plasma light intensity calculation unit 120A excludes 10% of the light intensities of the respective wavelengths in descending order of a distance from the applied nine-dimensional polynomial. The light intensities of the respective wavelengths are indicated by (a) the straight line 1004 in the third wavelength band and (b) the spectroscopic spectrum 400 in the wavelength band other than the third wavelength band. It should be noted that the rate of the excluded light intensity is not limited to 10%, but may be other rate.

The plasma light intensity calculation unit 120A re-performs the polynomial approximation on (a) the light intensity that is calculated for the third wavelength band excluded at S26 and (b) the spectroscopic spectrum in the wavelength band other than the third wavelength band (S28). More specifically, the plasma light intensity calculation unit 120A applies, for example, a nine-dimensional polynomial to the light intensity excluded at S26, among the light intensities of the respective wavelengths indicated by (a) the straight line 1004 in the third wavelength band and (b) the spectroscopic spectrum 400 in the wavelength band other than the third wavelength band. It should be noted that S26 and S28 may be eliminated.

Referring again to FIG. 7, the molecular light intensity calculation unit 130 subtracts, for each wavelength, the light intensity of the light emitted by the plasma as calculated by the plasma light intensity calculation unit 120A from the light intensity indicated by the spectroscopic spectrum so as to calculate a light intensity of light emitted by a molecule in a thin film formed on/above the substrate (S4).

For example, referring to FIG. 10, the molecular light intensity calculation unit 130 subtracts, for each wavelength, a light intensity indicated by the waveform 1004 from a light intensity indicated by the spectroscopic spectrum 400, thereby obtaining waveforms 1006 and 1008. The waveform 1006 indicates a light intensity of light emitted by the molecule of the thin film in the wavelength band other than the third wavelength band. The waveform 1008 indicates the light intensity of the light emitted by the molecule of the thin film in the third wavelength band. In FIG. 10, the waveform 1008 is shown as darker than the waveform 1006.

Finally, the ratio calculation unit 140 calculates, by using the light intensities calculated by the molecular light intensity calculation unit 130, a ratio between a peak value of a molecular spectrum of the first molecule (namely, a first kind of molecules) and a peak value of a molecular spectrum of the second molecule (namely, the second kind of molecules) (S6). For example, in the same manner as described in Embodiment 1, the ratio calculation unit 140 calculates a ratio between a light intensity of SiH* and a light intensity of Hα. It should be noted that the calculated ratio is not limited to the above. For example, it is also possible to calculate a ratio between a light intensity of SiH* and a light intensity of Si*.

The plasma light emission analyzing device 100A according to Embodiment 2 as described above has the following effects.

The spectroscopic spectrum measured by the spectrometer 200 includes a spectroscopic spectrum of plasma and a spectroscopic spectrum of a molecule in a thin film formed on/above the substrate. Therefore, the spectroscopic spectrum measured by the spectrometer 200 has a greater light intensity at a wavelength corresponding to the molecule in the thin film formed on/above the substrate. There is therefore the situation where, when polynomial approximation is performed on the spectroscopic spectrum measured by the spectrometer 200, due to values of the spectroscopic spectrum of the molecule in the thin film formed on/above the substrate, it is impossible to correctly calculate, for each wavelength, the light intensity of the light emitted by the plasma. However, the plasma light emission analyzing device 100A according to Embodiment 2 calculates a light intensity of light in the third wavelength band based on the first wavelength band and the second wavelength band having the third wavelength band therebetween. Therefore, the plasma light emission analyzing device 100A according to Embodiment 2 is capable of correctly calculating the spectroscopic spectrum of the plasma. As a result, it is possible to correctly calculate a light intensity of light emitted by a molecule in a thin film formed on/above the substrate, and eventually correctly calculate a ratio of light emission intensities between specific two kinds of molecules.

In addition, since a light intensity having a large difference from an applied polynomial is excluded, it is possible to correctly calculate a spectroscopic spectrum of plasma after removing influence of noises.

(Variation of Embodiment 2)

The plasma light emission analyzing device 100A according to Embodiment 2 calculates, as shown in FIG. 10, a difference between (a) the waveform 1002 generated by performing polynomial approximation on (a-1) the straight line 1004 in the third wavelength band and (a-2) the spectroscopic spectrum 400 in the wavelength band other than the third wavelength band and (b) the spectroscopic spectrum 400 so as to calculate a light intensity of light emitted by a molecule in a thin film formed on/above the substrate.

Figure 11:
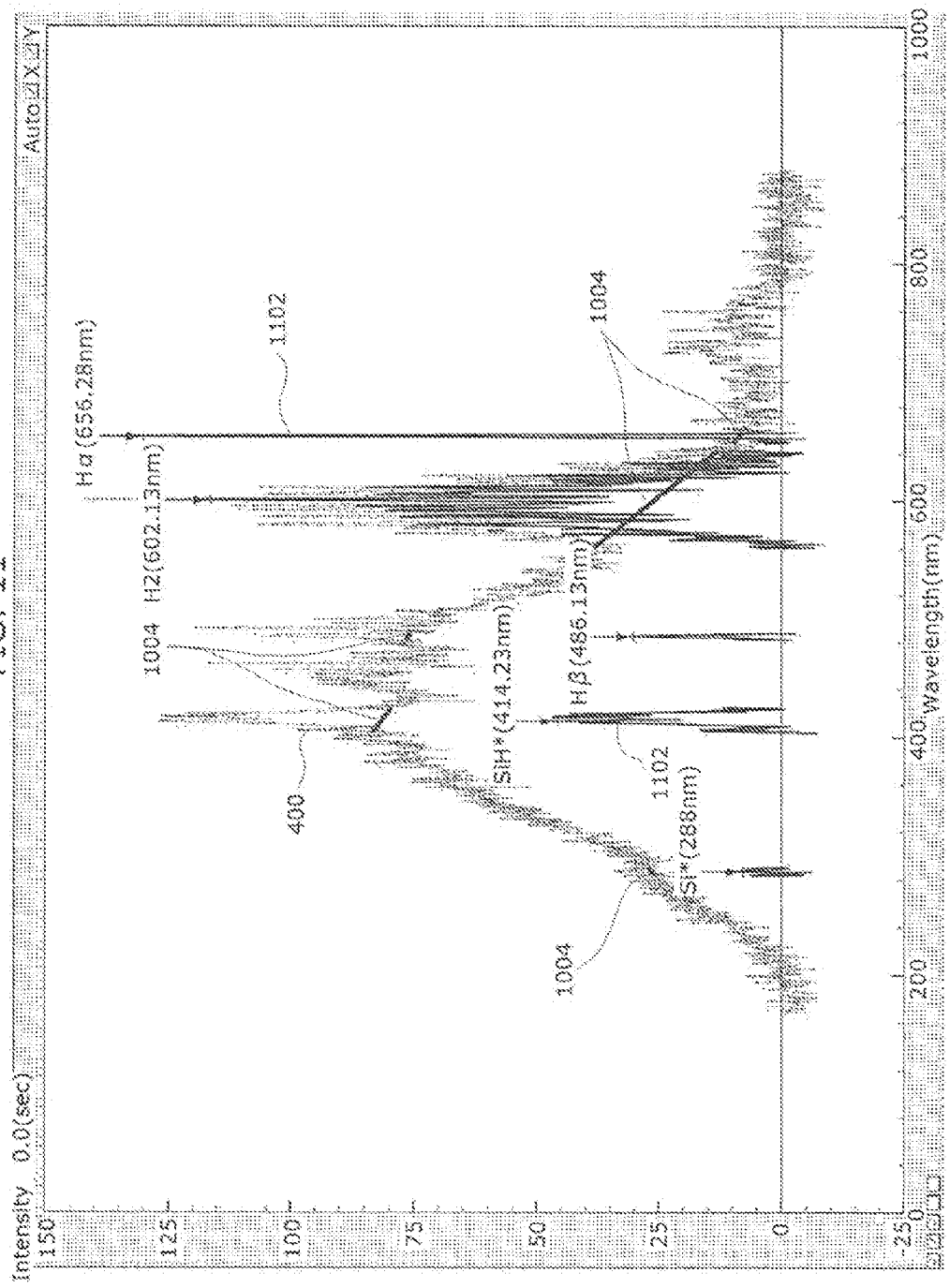
FIG. 11 is a graph for explaining processing performed by a plasma light emission analyzing device according to a variation of Embodiment 2 of the present invention.

However, the waveform 1002 is not necessarily calculated. For example, as shown in FIG. 11, it is also possible that the molecular light intensity calculation unit 130 subtracts, for each wavelength in the third wavelength band, a light intensity of light in the third wavelength band as calculated by the plasma light intensity calculation unit 120A and shown by the straight line 1004, from a light intensity indicated by the spectroscopic spectrum 400 so as to calculate a light intensity of light emitted by a molecule in a thin film formed on/above the substrate. The waveform 1102 is a waveform generated by subtracting the light intensity indicated by the straight line 1004 from the spectroscopic spectrum 400.

Although the embodiments of the plasma light emission analyzing system have been described as above, the present invention is not limited to the embodiments.

Figure 12:
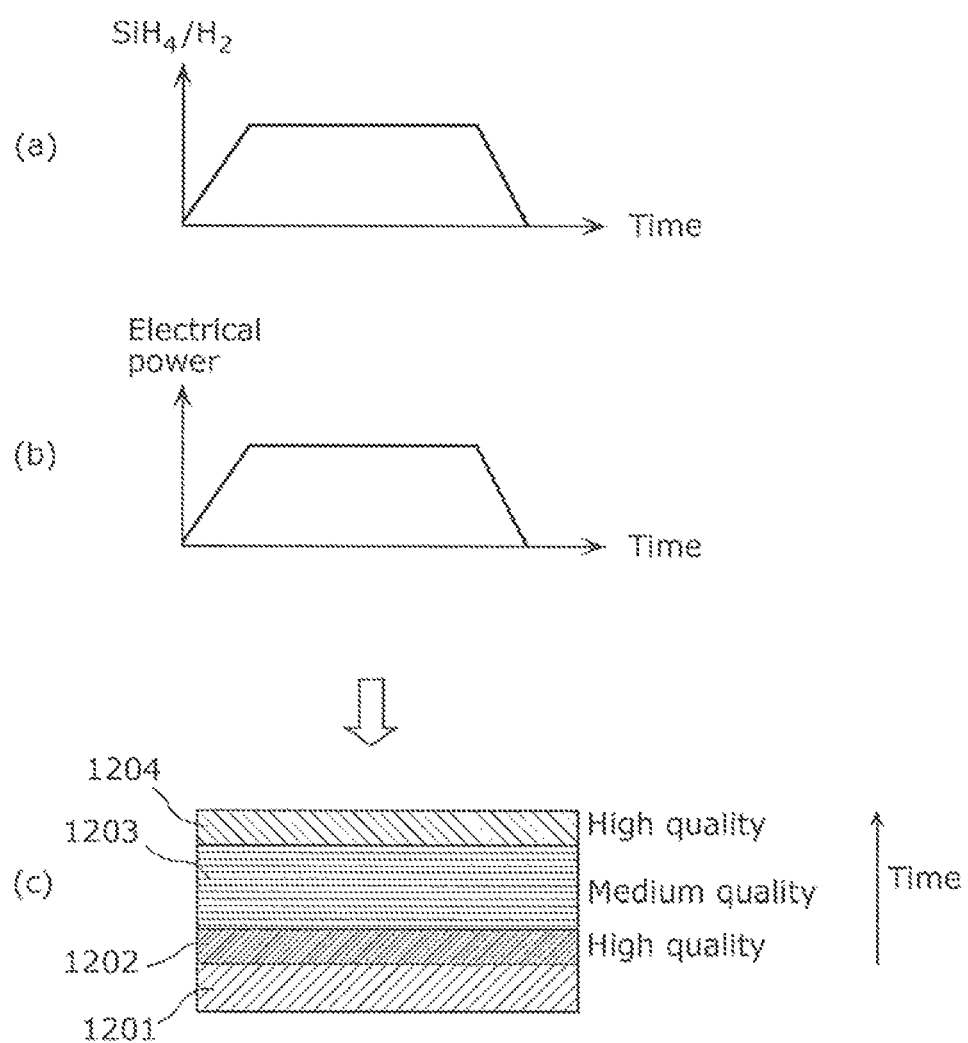
FIG. 12 shows diagrams for explaining feedback of analysis results of the plasma light emission analyzing device to a plasma CVD device.

For example, it is also possible that the ratio calculated by the plasma light emission analyzing device 100 or 100A is fed back to the plasma CVD device 210 to control a flow rate of a material gas. The plasma CVD device 210 causes a ratio between $SiH_4$ and $H_2$ to vary with time as shown in (a) in FIG. 12, and causes also a power for driving the plasma CVD device 210 to vary with time as shown in (b) in FIG. 12. More specifically, in starting film forming on the substrate, a ratio of $SiH_4$ is gradually increased and a power is also gradually increased. Thereby, as shown in (c) in FIG. 12, a high-quality thin film 1202 is formed on the substrate 1201 at a low speed. After that, the ratio of $SiH_4$ is kept high, and the power is also kept high. As a result, a medium-quality thin film 1203 is formed on the thin film 1202 at a high speed. Finally, the ratio of $SiH_4$ is gradually decreased, and the power is also gradually decreased. Thereby, a high-quality thin film 1204 is formed on the thin film 1203 at a low speed.

It should be noted that it has been described in Embodiments 1 and 2 that application of a nine-dimensional polynomial to a spectroscopic spectrum is performed as an example to calculate, for each wavelength, a light intensity of light emitted by plasma. However, the function to be applied is not limited to a nine-dimensional polynomial. It is also possible to apply a polynomial with other degree order, or apply a function other than a polynomial.

It should also be noted that Embodiments 1 and 2 have been given for the plasma light emission analyzing devices 100 and 100A, respectively, each of which calculates a ratio of light emission intensities of two kinds of molecules or atoms in a thin film formed on/above the substrate in the plasma CVD device 210. However, an application target of the present invention is not limited to the plasma CVD device 210. For example, if the same method as performed by the plasma CVD device 210 is applied to other devices, such as spattering devices, etching devices, and sterilization monitoring devices, which need to calculate a ratio of light emission intensities between specific two kinds of molecules or atoms in a container, it is possible to calculate the ratio.

For example, the first light intensity calculation unit performs polynomial approximation on a spectroscopic spectrum indicating a light intensity for each wavelength in a sterilization monitoring device as measured by the spectrometer 200 so as to calculate the light intensity for each wavelength in the sterilization monitoring. Next, the second light intensity calculation unit subtracts, for each wavelength, the light intensity calculated by the first light intensity calculation unit from the light intensity indicated by the spectroscopic spectrum so as to calculate a light intensity corresponding to a bright-line spectrum of a molecule or an atom. Furthermore, the ratio calculation unit calculates, by using the light intensity corresponding to the bright-line spectrum of a molecule or an atom as calculated by the second light intensity calculation unit, a ratio between (a) a peak value of a molecular spectrum of a first molecule or an atomic spectrum of a first atom and (b) a peak value of a molecular spectrum of a second molecule or an atomic spectrum of a second atom. By the above processing, it is possible to calculate a ratio of light emission intensities between two kinds of molecules or atoms in the spectrometer 200.

Each of the plasma light emission analyzing device 100 and the plasma light emission analyzing device 100A described above may be a computer system including a microprocessor, a Read Only Memory (ROM), a Random Access Memory (RAM), a hard disk unit, a display unit, a keyboard, a mouse, and the like. The RAM or the hard disk unit holds a computer program. The microprocessor operates according to the computer program, thereby casing each of the plasma light emission analyzing devices to perform its functions. Here, the computer program consists of combinations of instruction codes for issuing instructions to the computer to execute predetermined functions.

It should also be noted that a part or all of the structural elements included in each of the plasma light emission analyzing devices may be implemented into a single Large Scale Integration (LSI). The system LSI is a super multi-function LSI that is a single chip into which a plurality of structural elements are integrated. More specifically, the system LSI is a computer system including a microprocessor, a ROM, a RAM, and the like. The RAM holds a computer program. The microprocessor operates according to the computer program to cause the system LSI to perform its functions.

It should also be noted that a part or all of the structural elements included in each of the plasma light emission analyzing devices may be implemented into an Integrated Circuit (IC) card or a single module which is attachable to and removable from the device. The IC card or the module is a computer system including a microprocessor, a ROM, a RAM, and the like. The IC card or the module may include the above-described super multi-function LSI. The microprocessor operates according to the computer program to cause the IC card or the module to perform its functions. The IC card or the module may have tamper resistance.

It should also be noted that the present invention may be the above-described method. The present invention may be a computer program causing a computer to execute the method, or digital signals indicating the computer program.

It should also be noted that the present invention may be a non-transitory computer-readable recording medium on which the computer program or the digital signals are recorded. Examples of the computer-readable recording medium are a flexible disk, a hard disk, a Compact Disc (CD)-ROM, a magnetooptic disk (MO), a Digital Versatile Disc (DVD), a DVD-ROM, a DVD-RAM, a BD (Blue-ray®) Disc), and a semiconductor memory. The present invention may be digital signals recorded on the non-transitory recording medium.

It should also be noted in the present invention that the computer program or the digital signals may be transmitted via an electric communication line, a wired or wireless communication line, a network represented by the Internet, data broadcasting, and the like.

It should also be noted that the present invention may be a computer system including a microprocessor operating according to the computer program and a memory storing the computer program.

It should also be noted that the program or the digital signals may be recorded onto the non-transitory recording medium to be transferred, or may be transmitted via a network or the like, so that the program or the digital signals can be executed by a different independent computer system.

It should also be noted that the above-described embodiments and their variations may be combined.

The disclosed embodiments are merely exemplary and do not limit the present invention. The scope of the present invention is indicated not by the above description but by the appended claims. Accordingly, all modifications are intended to be included within the same meanings and the scope of the claims.

INDUSTRIAL APPLICABILITY

The present invention is applicable to plasma light emission analyzing devices, and more particularly to plasma light emission analyzing devices and the like which analyze a light emission state of plasma in a plasma CVD device that manufactures semiconductor substrates for solar batteries.

REFERENCE SIGNS LIST 100, 100A plasma light emission analyzing device
110 wavelength obtainment unit
120, 120A plasma light intensity calculation unit
130 molecular light intensity calculation unit
140 ratio calculation unit
200 spectrometer
210 plasma CVD device
300 display device
400, 802, 804, 806 spectroscopic spectrum
402, 404, 1002, 1006, 1008, 1102 waveform
808, 1004 straight line

The invention claimed is:
1. A light emission analyzing device comprising:
a first light intensity calculation unit configured to perform polynomial approximation on a spectroscopic spectrum indicating a light intensity for each wavelength in a container as measured by a spectrometer so as to calculate the light intensity, the first light intensity calculation unit performing the polynomial approximation on the spectroscopic spectrum indicating the light intensity for each wavelength in the container in a plasma Chemical Vapor Deposition (CVD) device as measured by the spectrometer so as to calculate, for each wavelength, a light intensity of light emitted by plasma in the plasma CVD device;

a second light intensity calculation unit configured to subtract, for each wavelength, the light intensity calculated by the first light intensity calculation unit from the light intensity indicated by the spectroscopic spectrum measured by the spectrometer so as to calculate a light intensity corresponding to a bright-line spectrum of a molecule or an atom, the second light intensity calculation unit subtracting, for each wavelength, the light intensity of the light emitted by the plasma as calculated by the first light intensity calculation unit, from the light intensity indicated by the spectroscopic spectrum measured by the spectrometer so as to calculate a light intensity of light emitted by a molecule or an atom in a thin film formed above a substrate, and the light intensity of the light emitted by the molecule or the atom corresponding to the bright-line spectrum of the molecule or the atom;

a ratio calculation unit configured to calculate, by using the light intensity calculated by the second light intensity calculation unit, a ratio between (a) a peak value of a molecular spectrum of a first molecule or an atomic spectrum of a first atom and (b) a peak value of a molecular spectrum of a second molecule or an atomic spectrum of a second atom; and a wavelength obtainment unit configured to obtain: a first wavelength; a second wavelength longer than the first wavelength; a third wavelength longer than the second wavelength; and a fourth wavelength longer than the third wavelength, wherein the first light intensity calculation unit is configured to (a) apply a predetermined function to (a-1) a spectroscopic spectrum included in a first wavelength band having the first wavelength to the second wavelength in the spectroscopic spectrum measured by the spectrometer and (a-2) a spectroscopic spectrum included in a second wavelength band having the third wavelength to the fourth wavelength in the spectroscopic spectrum measured by the spectrometer so as to calculate a light intensity of light in a third wavelength band that is a wavelength band from a first predetermined wavelength included in the first wavelength band to a second predetermined wavelength included in the second wavelength band, and (b) perform the polynomial approximation on (b-1) the light intensity calculated for the third wavelength band and (b-2) a spectroscopic spectrum in a wavelength band other than the third wavelength band so as to calculate the light intensity for each wavelength in the container.

2. The light emission analyzing device according to claim 1, wherein the first light intensity calculation unit is configured to (a) apply a straight line to a spectroscopic spectrum included in the first wavelength band having the first wavelength to the second wavelength in the spectroscopic spectrum measured by the spectrometer so as to calculate a first straight line, (b) apply a straight line to a spectroscopic spectrum included in the second wavelength band having the third wavelength to the fourth wavelength in the spectroscopic spectrum measured by the spectrometer so as to calculate a second straight line, and (c) generate a straight line from a point on the first predetermined wavelength on the first straight line to a point on the second predetermined wavelength on the second straight line so as to calculate a light intensity of light in the third wavelength band.

3. The light emission analyzing device according to claim 2, wherein the first predetermined wavelength is (the first wavelength+the second wavelength)/2, and
the second predetermined wavelength is (the third wavelength+the fourth wavelength)/2.

4. The light emission analyzing device according to claim 1, wherein the first light intensity calculation unit is further configured to (a) exclude a predetermined percentage of light intensities of respective wavelengths in descending order of a difference from a polynomial applied in the polynomial approximation, and (b) re-perform the polynomial approximation on (b-1) the light intensity calculated for the third wavelength band and (b-2) the spectroscopic spectrum in the wavelength band other than the third wavelength band.

5. The light emission analyzing device according to claim 1, wherein the first predetermined wavelength is the second wavelength, and
the second predetermined wavelength is the third wavelength.

6. A light emission analyzing device comprising:

a first light intensity calculation unit configured to perform polynomial approximation on a spectroscopic spectrum indicating a light intensity for each wavelength in a container as measured by a spectrometer so as to calculate the light intensity, the first light intensity calculation unit performing the polynomial approximation on the spectroscopic spectrum indicating the light intensity for each wavelength in the container in a plasma Chemical Vapor Deposition (CVD) device as measured by the spectrometer so as to calculate, for each wavelength, a light intensity of light emitted by plasma in the plasma CVD device;

a second light intensity calculation unit configured to subtract, for each wavelength, the light intensity calculated by the first light intensity calculation unit from the light intensity indicated by the spectroscopic spectrum measured by the spectrometer so as to calculate a light intensity corresponding to a bright-line spectrum of a molecule or an atom, the second light intensity calculation unit subtracting, for each wavelength, the light intensity of the light emitted by the plasma as calculated by the first light intensity calculation unit, from the light intensity indicated by the spectroscopic spectrum measured by the spectrometer so as to calculate a light intensity of light emitted by a molecule or an atom in a thin film formed above a substrate, and the light intensity of the light emitted by the molecule or the atom corresponding to the bright-line spectrum of the molecule or the atom;

a ratio calculation unit configured to calculate, by using the light intensity calculated by the second light intensity calculation unit, a ratio between (a) a peak value of a molecular spectrum of a first molecule or an atomic spectrum of a first atom and (b) a peak value of a molecular spectrum of a second molecule or an atomic spectrum of a second atom; and a wavelength obtainment unit configured to obtain: a first wavelength; a second wavelength longer than the first wavelength; a third wavelength longer than the second wavelength; and a fourth wavelength longer than the third wavelength, wherein the first light intensity calculation unit is configured to apply a predetermined function to (a) a spectroscopic spectrum included in a first wavelength band having the first wavelength to the second wavelength in the spectroscopic spectrum measured by the spectrometer and (b) a spectroscopic spectrum included in a second wavelength band having the third wavelength to the fourth wavelength in the spectroscopic spectrum measured by the spectrometer so as to calculate a light intensity of light in a third wavelength band that is a wavelength band from a first predetermined wavelength included in the first wavelength band to a second predetermined wavelength included in the second wavelength band, and the second light intensity calculation unit is configured to subtract, for each wavelength in the third wavelength band, the light intensity calculated by the first light intensity calculation unit from the light intensity indicated by the spectroscopic spectrum measured by the spectrometer so as to calculate the light intensity corresponding to the bright-line spectrum of the molecule or the atom.

7. The light emission analyzing device according to claim 6, wherein the first light intensity calculation unit is configured to (a) apply a straight line to a spectroscopic spectrum included in the first wavelength band having the first wavelength to the second wavelength in the spectroscopic spectrum measured by the spectrometer so as to calculate a first straight line, (b) apply a straight line to a spectroscopic spectrum included in the second wavelength band having the third wavelength to the fourth wavelength in the spectroscopic spectrum measured by the spectrometer so as to calculate a second straight line, and (c) generate a straight line from a point on the first predetermined wavelength on the first straight line to a point on the second predetermined wavelength on the second straight line so as to calculate a light intensity of light in the third wavelength band.

8. The light emission analyzing device according to claim 7, wherein the first predetermined wavelength is (the first wavelength+the second wavelength)/2, and the second predetermined wavelength is (the third wavelength+the fourth wavelength)/2.

9. The light emission analyzing device according to claim 6, wherein the first predetermined wavelength is the second wavelength, and the second predetermined wavelength is the third wavelength.

10. A light emission analyzing method comprising:

performing polynomial approximation on a spectroscopic spectrum indicating a light intensity for each wavelength in a container as measured by a spectrometer so as to calculate the light intensity, wherein in the performing of the polynomial approximation, the polynomial approximation is performed on the spectroscopic spectrum indicating the light intensity for each wavelength in the container in a plasma Chemical Vapor Deposition (CVD) device as measured by the spectrometer so as to calculate, for each wavelength, a light intensity of light emitted by plasma in the plasma CVD device;

subtracting, for each wavelength, the light intensity calculated in the performing of the polynomial approximation from the light intensity indicated by the spectroscopic spectrum measured by the spectrometer so as to calculate a light intensity corresponding to a bright-line spectrum of a molecule or an atom, wherein in the subtracting, for each wavelength, the light intensity of the light emitted by the plasma as calculated in the performing of the polynomial approximation is subtracted from the light intensity indicated by the spectroscopic spectrum measured by the spectrometer so as to calculate a light intensity of light emitted by a molecule or an atom in a thin film formed above a substrate, and the light intensity of the light emitted by the molecule or the atom corresponds to the bright-line spectrum of the molecule or the atom;

calculating, by using the light intensity calculated in the subtracting, a ratio between (a) a peak value of a molecular spectrum of a first molecule or an atomic spectrum of a first atom and (b) a peak value of a molecular spectrum of a second molecule or an atomic spectrum of a second atom; and obtaining: a first wavelength; a second wavelength longer than the first wavelength; a third wavelength longer than the second wavelength; and a fourth wavelength longer than the third wavelength, wherein the performing of the polynomial approximation includes (a) applying a predetermined function to (a-1) a spectroscopic spectrum included in a first wavelength band having the first wavelength to the second wavelength in the spectroscopic spectrum measured by the spectrometer and (a-2) a spectroscopic spectrum included in a second wavelength band having the third wavelength to the fourth wavelength in the spectroscopic spectrum measured by the spectrometer so as to calculate a light intensity of light in a third wavelength band that is a wavelength band from a first predetermined wavelength included in the first wavelength band to a second predetermined wavelength included in the second wavelength band, and (b) performing the polynomial approximation on (b-1) the light intensity calculated for the third wavelength band and (b-2) a spectroscopic spectrum in a wavelength band other than the third wavelength band so as to calculate the light intensity for each wavelength in the container.

11. A non-transitory computer-readable recording medium for use in a computer, the recording medium having a computer program recorded thereon for causing the computer to execute the light emission analyzing method according to claim 10.

12. A light emission analyzing method comprising:

performing polynomial approximation on a spectroscopic spectrum indicating a light intensity for each wavelength in a container as measured by a spectrometer so as to calculate the light intensity, wherein in the performing of the polynomial approximation, the polynomial approximation is performed on the spectroscopic spectrum indicating the light intensity for each wavelength in the container in a plasma Chemical Vapor Deposition (CVD) device as measured by the spectrometer so as to calculate, for each wavelength, a light intensity of light emitted by plasma in the plasma CVD device;

subtracting, for each wavelength, the light intensity calculated by the performing of the polynomial approximation from the light intensity indicated by the spectroscopic spectrum measured by the spectrometer so as to calculate a light intensity corresponding to a bright-line spectrum of a molecule or an atom, wherein in the subtracting, for each wavelength, the light intensity of the light emitted by the plasma as calculated in the performing of the polynomial approximation is subtracted from the light intensity indicated by the spectroscopic spectrum measured by the spectrometer so as to calculate a light intensity of light emitted by a molecule or an atom in a thin film formed above a substrate, the light intensity of the light emitted by the molecule or the atom corresponding to the bright-line spectrum of the molecule or the atom;

calculating, by using the light intensity calculated in the subtracting, a ratio between (a) a peak value of a molecular spectrum of a first molecule or an atomic spectrum of a first atom and (b) a peak value of a molecular spectrum of a second molecule or an atomic spectrum of a second atom; and obtaining: a first wavelength; a second wavelength longer than the first wavelength; a third wavelength longer than the second wavelength; and a fourth wavelength longer than the third wavelength, wherein the performing of the polynomial approximation includes applying a predetermined function to (a) a spectroscopic spectrum included in a first wavelength band having the first wavelength to the second wavelength in the spectroscopic spectrum measured by the spectrometer and (b) a spectroscopic spectrum included in a second wavelength band having the third wavelength to the fourth wavelength in the spectroscopic spectrum measured by the spectrometer so as to calculate a light intensity of light in a third wavelength band that is a wavelength band from a first predetermined wavelength included in the first wavelength band to a second predetermined wavelength included in the second wavelength band, and the subtracting includes subtracting, for each wavelength in the third wavelength band, the light intensity calculated in the performing of the polynomial approximation from the light intensity indicated by the spectroscopic spectrum measured by the spectrometer so as to calculate the light intensity corresponding to the bright-line spectrum of the molecule or the atom.

13. A non-transitory computer-readable recording medium for use in a computer, the recording medium having a computer program recorded thereon for causing the computer to execute the light emission analyzing method according to claim 12.

* * * * *